United States Patent
Boyd et al.

(10) Patent No.: US 7,179,818 B2
(45) Date of Patent: Feb. 20, 2007

(54) SUBSTITUTED AMINOQUINUCLIDINE COMPOUNDS

(75) Inventors: Robert E. Boyd, Horsham, PA (US); Allen B. Reitz, Lansdale, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 371 days.

(21) Appl. No.: 10/684,537

(22) Filed: Oct. 14, 2003

(65) Prior Publication Data

US 2004/0110789 A1    Jun. 10, 2004

Related U.S. Application Data

(60) Provisional application No. 60/418,603, filed on Oct. 15, 2002.

(51) Int. Cl.
*A61K 31/44* (2006.01)

(52) U.S. Cl. .................. 514/305; 546/134; 546/135

(58) Field of Classification Search ............... 546/134, 546/135; 514/305
See application file for complete search history.

(56) References Cited

FOREIGN PATENT DOCUMENTS

| WO | WO 99/33806 A1 | 7/1999 |
|---|---|---|
| WO | WO 01/46191 A1 | 6/2001 |

OTHER PUBLICATIONS

Dondio, Development of novel pain relief agents acting through the selective activation of the delta-opioid receptor, II Farmaco 55 (2000) 178-180.*
PCT International Search Report, dated Apr. 22, 2004, for PCT Int'l. Appln. No. PCT/US03/32221.

* cited by examiner

*Primary Examiner*—Amelia A. Owens
(74) *Attorney, Agent, or Firm*—John Harbour

(57) ABSTRACT

This invention is directed towards substituted aminoquinuclidine compounds useful as delta-opioid receptor modulators, delta-opioid receptor agonists useful as analgesics and delta-opioid receptor antagonists useful as immunosuppressants, antiinflammatory agents, agents for the treatment of neurological and psychiatric conditions, medicaments for drug and alcohol abuse, agents for treating gastritis and diarrhea, cardiovascular agents and agents for the treatment of respiratory diseases.

25 Claims, No Drawings

SUBSTITUTED AMINOQUINUCLIDINE COMPOUNDS

CROSS REFERENCE TO RELATED APPLICATIONS

This application claims priority of U.S. non-provisional application No. 60/418,603, filed Oct. 15, 2002. The complete disclosure of the aforementioned related U.S. patent application is hereby incorporated by reference for all purposes.

FIELD OF THE INVENTION

The present invention is directed to delta-opioid receptor modulators and methods for use thereof. More particularly, the present invention is directed to substituted aminoquinuclidine compounds which are delta-opioid receptor modulators, agonists or antagonists and methods for their use.

BACKGROUND OF THE INVENTION

WO 97/23466 discloses compounds described as having an analgesic effect, having a general and a typical preferred formula:

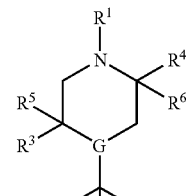

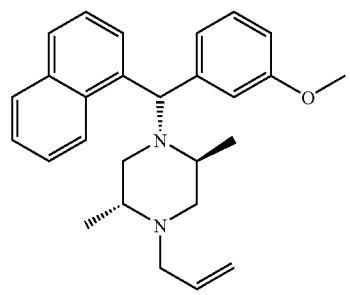

WO 98/28275 further discloses compounds described as having an analgesic effect, having a general and a typical preferred formula:

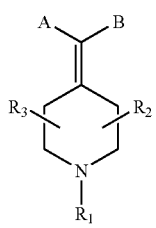

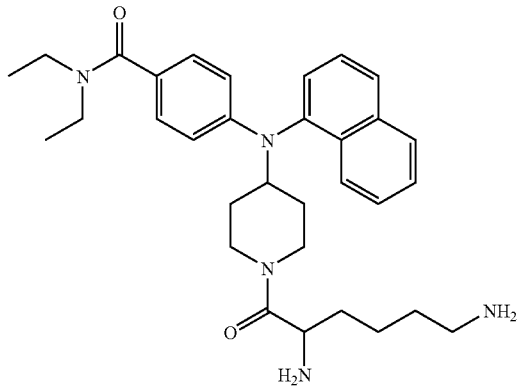

WO 93/15062 discloses compounds which have been described as delta-opioid and mu-opioid receptor agonists, having (approximately) the formula:

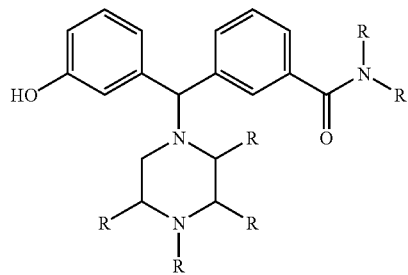

Astra Aktiebolag, World Patent 98/28270 discloses compounds with analgesic activity mediated through the delta opiate receptor having the general formula:

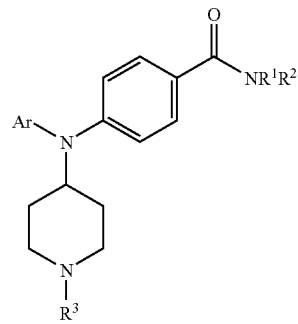

The synthesis and binding affinities for 4-diarylaminotropane compounds of the general formula:

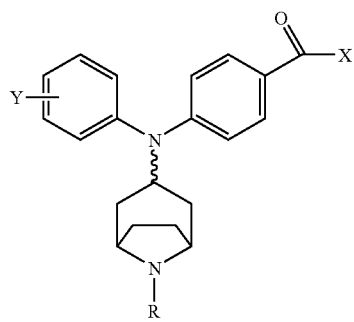

wherein R is hydrogen, methyl, propyl, hexyl, 2-ethylbutyl, allyl, 3,3-dimethallyl, cyclohexylmethyl, phenethyl, phenyl-propyl, 2,2-diphenylethyl, 3,4-dimethoxyphenethyl, 4-fluorophenethyl, 2-furylmethyl; 3,4-methylenedioxybenzyl, cyano and X is N,N-dimethylamino, N,N-diethylamino, N,N-dipropylamino, N-methyl,N-ethylamino, N-methyl,N-propylamino, N-methyl,N-phenylamino, N-ethyl,N-(4-methyl)benzylamino, N-butyl,N-ethylamino, N-butyl,N-propylamino, [N-ethyl,N-(2-methyl)allyl]amino, hydroxy, O-t-butyl and 1-pyrrolidinyl; and, Y is hydrogen, methoxy and methylthio as δ-opioid agonists have been described (Boyd, R. E., Carson, J. R., Codd, E. E., Gauthier, A. D., Neilson, L. A and Zhang, S-P., *Bioorg. Med. Chem. Lett.*, 2000, 10: 1109–1111).

The 4-[aryl(8-azabicyclo[3.2.1]octan-3-yl)]aminobenzoic acid derivatives disclosed in the above reference are claimed as δ-opioid receptor modulators in World Patent 01/46191.

4-[(8-Alkyl-8-azabicyclo[3.2.1]octyl-3-yl)-3-arylanilino]-N,N-diethylbenzamides have also been described as selective δ-opioid ligands (Thomas, J. B., Atkinson, R. N., Rothman, R. B., Burgess, J. P., Mascarella, S. W., Dersch, C. M., Xu, H. and Carroll, F. I., *Bioorg. Med. Chem. Lett.*, 2000, 10: 1281–1284).

In addition, 3-(diarylmethylene)-8-azabicyclo[3.2.1]octanes are described as δ- and μ-receptor modulators in World Patent 01/66543.

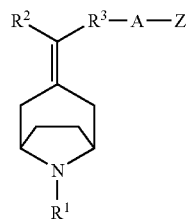

The foregoing reference compounds have been described as either δ-opioid or μ-opioid receptor agonists or antagonists.

The substituted aminoquinuclidine derivatives of the present invention have not been previously described as δ-opioid receptor modulators.

It is an object of the present invention to provide substituted aminoquinuclidine compounds which are delta-opioid receptor modulators. It is also an object of the present invention to provide substituted aminoquinuclidine compounds which are δ-opioid receptor agonists useful as analgesics. It is another object of the present invention to provide δ-opioid receptor antagonists useful for treating immune disorders, inflammation, neurological conditions, psychiatric conditions, drug abuse, alcohol abuse, gastritis, diarrhea, cardiovascular disorders or respiratory disorders. It is a further object of the present invention to provide a method for treating a disorder modulated by the δ-opioid receptor.

SUMMARY OF THE INVENTION

The present invention provides substituted aminoquinuclidine compounds of Formula (I):

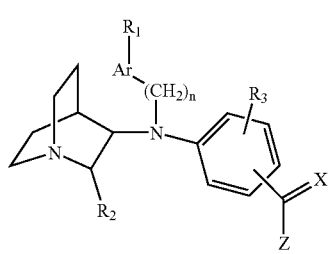

Formula (I)

wherein:

Ar is selected from the group consisting of aryl and heteroaryl;

n is an integer from 0 to 2;

$R_1$ is one to three substituents independently selected from the group consisting of hydrogen, $C_{1-8}$alkyl, $C_{2-8}$alkenyl, $C_{2-8}$alkynyl, $C_{3-8}$cycloalkyl, aryl($C_{1-8}$)alkyl, $C_{1-8}$alkoxy, aryloxy, aryl($C_{1-8}$)alkoxy, $C_{1-8}$alkylthio, trifluoro($C_{1-8}$)alkyl, trifluoro($C_{1-8}$)alkoxy, amino, —NH($C_{1-8}$)alkyl, —N[($C_{1-8}$)alkyl]$_2$, —NH(aryl), —N(aryl)$_2$, —NH($C_{1-8}$)alkylaryl, —N[($C_{1-8}$)alkylaryl]$_2$, —CO$_2$H, —CO$_2$($C_{1-8}$)alkyl, —CO$_2$(aryl), —C(O)NH$_2$, —C(O)NH($C_{1-8}$)alkyl, —C(O)N[($C_{1-8}$)alkyl]$_2$, —NHC(O)($C_{1-8}$)alkyl, —SO$_2$H, —SO$_2$($C_{1-8}$)alkyl, —SO$_2$NH$_2$, —SO$_2$NH($C_{1-8}$)alkyl, —SO$_2$N[($C_{1-8}$)alkyl]$_2$, —C(O)($C_{1-8}$)alkyl, —C(O)aryl, —C(O)($C_{1-8}$)alkylaryl, aryl, heteroaryl, heterocyclyl, halogen, hydroxy, cyano, and nitro;

$R_2$ is selected from the group consisting of hydrogen and $C_{1-8}$alkyl;

$R_3$ is selected from the group consisting of hydrogen, $C_{1-8}$alkyl, $C_{1-8}$alkoxy, $C_{1-8}$alkylthio, trifluoro($C_{1-8}$)alkyl, trifluoro($C_{1-8}$)alkoxy, amino, —NH($C_{1-8}$)alkyl, —N[($C_{1-8}$)alkyl]$_2$, —CO$_2$H, —CO$_2$($C_{1-8}$)alkyl, —C(O)NH$_2$, —C(O)NH($C_{1-8}$)alkyl, —C(O)N[($C_{1-8}$)alkyl]$_2$, —NHC(O)($C_{1-8}$)alkyl, —SO$_2$H, —SO$_2$($C_{1-8}$)alkyl, —SO$_2$NH$_2$, —SO$_2$NH($C_{1-8}$)alkyl, —SO$_2$N[($C_{1-8}$)alkyl]$_2$, —C(O)($C_{1-8}$)alkyl, halogen, hydroxy, cyano, and nitro;

X is selected from the group consisting of S and O;

Z is N($R_4$)($R_5$) or is a 5- or 6-membered saturated, monocyclic, heterocyclic ring, wherein said heterocyclic ring contains one nitrogen member which is the point of attachment, optionally contains one additional heteroatom member of oxygen, sulfur or nitrogen and optionally contains a double bond between two ring members;

$R_4$ and $R_5$ are independently selected from the group consisting of hydrogen, $C_{1-8}$alkyl, hydroxy($C_{1-8}$)alkyl, $C_{2-8}$alkenyl, $C_{3-8}$cycloalkyl, aryl and aryl($C_{1-8}$)alkyl, wherein said cycloalkyl, aryl and the aryl portion of aryl($C_{1-8}$)alkyl are optionally substituted with one to three substituents independently selected from the group consisting of $C_{1-8}$alkyl, $C_{2-8}$alkenyl, $C_{1-8}$alkoxy, trifluoro($C_{1-8}$)alkyl, trifluoro($C_{1-8}$)alkoxy, $C_{3-8}$cycloalkyl and halogen; and, the moiety —C(X)Z is attached on the phenyl at the 3 or 4 position;

and pharmaceutically acceptable enantiomers, diastereomers and salts thereof.

DETAILED DESCRIPTION OF THE INVENTION

Embodiments of the present invention include those compounds selected from compounds of Formula (I) wherein, preferably, Ar is phenyl.

Embodiments of the present invention include those compounds selected from compounds of Formula (I) wherein, preferably, n is an integer from 0 to 1.

Embodiments of the present invention include those compounds selected from compounds of Formula (I) wherein, preferably, $R_1$ is one substituent.

Preferably, $R_1$ is independently selected from the group consisting of hydrogen, $C_{1-8}$alkyl, $C_{1-8}$alkoxy, $C_{1-8}$alkylthio, halogen, hydroxy, trifluoro($C_{1-8}$)alkyl and trifluoro($C_{1-8}$)alkoxy.

More preferably, $R_1$ is independently selected from the group consisting of hydrogen, $C_{1-4}$alkoxy, $C_{1-4}$alkylthio, halogen, hydroxy and trifluoro($C_{1-4}$)alkyl.

Most preferably, $R_1$ is independently selected from the group consisting of hydrogen, methoxy, methylthio, chlorine, fluorine, hydroxy and trifluoromethyl.

Embodiments of the present invention include those compounds selected from compounds of Formula (I) wherein, preferably, $R_2$ is selected from the group consisting of hydrogen and $C_{1-4}$alkyl.

More preferably, $R_2$ is selected from the group consisting of hydrogen and methyl.

Embodiments of the present invention include those compounds selected from compounds of Formula (I) wherein, preferably, $R_3$ is one or two substituents. More preferably, $R_3$ is one substituent.

Embodiments of the present invention include those compounds selected from compounds of Formula (I) wherein, preferably, $R_3$ is substituted at the 3, 4, or 5 position.

Embodiments of the present invention include those compounds selected from compounds of Formula (I) wherein, preferably, $R_3$ is selected from the group consisting of hydrogen, $C_{1-8}$alkyl, halogen, trifluoro($C_{1-8}$)alkyl and trifluoro($C_{1-8}$)alkoxy.

More preferably, $R_3$ is selected from the group consisting of hydrogen, $C_{1-4}$alkyl and halogen.

Most preferably, $R_3$ is selected from the group consisting of hydrogen, methyl and chlorine.

Embodiments of the present invention include those compounds selected from compounds of Formula (I) wherein, preferably, X is O.

Embodiments of the present invention include those compounds selected from compounds of Formula (I) wherein, preferably, Z is selected from the group consisting $N(R_4)(R_5)$ or pyrrolinyl, pyrrolidinyl, 2-imidazolinyl, imidazolidinyl, 2-pyrazolinyl, pyrazolidinyl, piperidinyl, morpholinyl, thiomorpholinyl, piperazinyl; wherein the point of attachment for the pyrrolinyl, pyrrolidinyl, 2-imidazolinyl, imidazolidinyl, 2-pyrazolinyl, pyrazolidinyl, piperidinyl, morpholinyl, thiomorpholinyl, piperazinyl ring at Z is a nitrogen ring atom.

More preferably, Z is selected from the group consisting of $N(R_4)(R_5)$, pyrrolidinyl and morpholinyl; wherein the point of attachment for the pyrrolidinyl and morpholinyl ring at Z is a nitrogen ring atom.

Embodiments of the present invention include those compounds selected from compounds of Formula (I) wherein, preferably, $R_4$ and $R_5$ are independently selected from the group consisting of hydrogen, $C_{1-4}$alkyl, hydroxy($C_{1-4}$)alkyl, $C_{2-4}$alkenyl, $C_{3-8}$cycloalkyl, aryl and aryl($C_{1-4}$)alkyl, wherein said cycloalkyl, aryl and the aryl portion of aryl($C_{1-8}$)alkyl are optionally substituted with one to three substituents independently selected from the group consisting of $C_{1-4}$alkyl, $C_{2-4}$alkenyl, $C_{1-4}$alkoxy, $C_{3-8}$cycloalkyl, halogen, trifluoro($C_{1-4}$)alkyl and trifluoro($C_{1-4}$)alkoxy.

More preferably, $R_4$ and $R_5$ are independently selected from the group consisting of hydrogen and $C_{1-4}$alkyl.

Most preferably, $R_4$ and $R_5$ are independently selected from the group consisting of hydrogen, methyl and ethyl.

Embodiments of the present invention include those compounds selected from compounds of Formula (I) wherein, preferably, the moiety —C(X)Z is substituted on the phenyl at the 4 position.

Exemplified compounds of Formula (I) of the present invention include compounds of Formula (Ia):

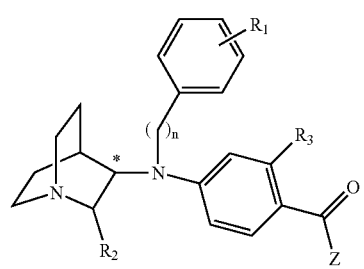

Formula (Ia)

wherein $R_1$, $R_2$, $R_3$, n and Z are selected from:

| Cpd | $R_1$ | $R_2$ | $R_3$ | n | Z | Configuration (*) |
|---|---|---|---|---|---|---|
| 1 | H | H | H | 0 | $N(Et)_2$ | — |
| 2 | 3-OMe | H | H | 0 | $N(Et)_2$ | — |
| 3 | 3-OH | H | H | 0 | $N(Et)_2$ | — |
| 4 | 3-$CF_3$ | H | H | 0 | $N(Et)_2$ | — |
| 5 | 2-OMe | H | H | 0 | $N(Et)_2$ | — |
| 6 | 3-Cl | H | H | 0 | $N(Et)_2$ | — |
| 7 | 3,5-diCl | H | H | 0 | $N(Et)_2$ | — |
| 8 | H | trans-Me | H | 0 | $N(Et)_2$ | — |
| 9 | H | cis-Me | H | 0 | $N(Et)_2$ | — |
| 10 | 3-SMe | trans-Me | H | 0 | $N(Et)_2$ | — |
| 11 | H | H | F | 0 | $N(Et)_2$ | — |
| 12 | H | H | Me | 0 | $N(Et)_2$ | — |
| 13 | H | H | Cl | 0 | $N(Et)_2$ | — |
| 14 | 4-OMe | H | H | 0 | 1-pyrrolidinyl | — |
| 15 | H | H | H | 0 | 4-morpholinyl | — |
| 16 | H | H | H | 1 | $N(Et)_2$ | — |
| 17 | 3-Cl | H | H | 1 | $N(Et)_2$ | — |
| 18 | 2-F | H | H | 1 | $N(Et)_2$ | — |
| 19 | 3-F | H | H | 1 | $N(Et)_2$ | — |
| 20 | H | H | H | 1 | $N(Et)_2$ | R |
| 21 | H | H | H | 1 | $N(Et)_2$ | S | and pharmaceutically acceptable enantiomers, diastereomers and salts thereof.

The compounds of the present invention may also be present in the form of pharmaceutically acceptable salts. For use in medicine, the salts of the compounds of this invention refer to non-toxic "pharmaceutically acceptable salts" (Ref. International J. Pharm., 1986, 33, 201–217; J. Pharm. Sci., 1997 (January), 66, 1, 1). Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

Where the compounds according to this invention are chiral, they may accordingly exist as enantiomers. In addition, the compounds may exist as diastereomers. It is to be understood that all such stereoisomers and racemic mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

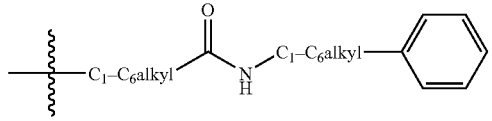

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The terms used in describing the invention are commonly used and known to those skilled in the art. However, the terms that could have other meanings are hereinafter defined. These definitions apply to the terms as they are used throughout this specification, unless otherwise limited in specific instances, either individually or as part of a larger group.

An "independently" selected substituent refers to a group of substituents, wherein the substituents may be different. Therefore, designated numbers of carbon atoms (e.g., $C_{1-8}$) shall refer independently to the number of carbon atoms in an alkyl or cycloalkyl moiety or to the alkyl portion of a larger substituent in which alkyl appears as its prefix root.

Unless specified otherwise, the term "alkyl" refers to a saturated straight or branched chain consisting solely of 1–8 hydrogen substituted carbon atoms; preferably, 1–6 hydrogen substituted carbon atoms; and, most preferably, 1–4 hydrogen substituted carbon atoms. The term "alkenyl" refers to a partially unsaturated straight or branched chain consisting solely of 2–8 hydrogen substituted carbon atoms that contains at least one double bond. The term "alkynyl" refers to a partially unsaturated straight or branched chain consisting solely of 2–8 hydrogen substituted carbon atoms that contains at least one triple bond. The term "alkoxy" refers to —O-alkyl, where alkyl is as defined supra. The term "hydroxyalkyl" refers to radicals wherein the alkyl chain terminates with a hydroxy radical of the formula HO-alkyl, where alkyl is as defined supra. Alkyl, alkenyl and alkynyl chains are optionally substituted within the alkyl chain or on a terminal carbon atom.

The term "cycloalkyl" refers to a saturated or partially unsaturated monocyclic alkyl ring consisting of 3–8 hydrogen substituted carbon atoms or a saturated or partially unsaturated bicyclic ring consisting of 9 or 10 hydrogen substituted carbon atoms. Examples include, and are not limited to, cyclopropyl, cyclopentyl, cyclohexyl or cycloheptyl.

The term "heterocyclyl" refers to a saturated or partially unsaturated ring having five or six members of which at least one member is a N, O or S atom and which optionally contains additional N, O or S atoms; a saturated or partially unsaturated bicyclic ring having nine or ten members of which at least one member is a N, O or S atom and which optionally contains additional N, O, or S atoms. Examples include, and are not limited to, pyrrolinyl, pyrrolidinyl, 1,3-dioxolanyl, imidazolinyl, imidazolidinyl, pyrazolinyl, pyrazolidinyl, piperidinyl, morpholinyl or piperazinyl.

The term "aryl" refers to phenyl, naphthalenyl, phenanthracenyl or anthracenyl.

The term "heteroaryl" refers to an aromatic monocyclic ring system containing five members of which at least one member is a N, O or S atom and which optionally contains one, two or three additional N atoms; an aromatic monocyclic ring having six members of which one, two or three members are a N atom; an aromatic bicyclic ring having nine members of which at least one member is a N, O or S atom and which optionally contains one, two or three additional N atoms; or, an aromatic bicyclic ring having ten members, of which one, two or three members are a N atom. Examples include, and are not limited to, furyl, thienyl, pyrrolyl, oxazolyl, thiazolyl, imidazolyl, pyrazolyl, isoxazolyl, isothiazolyl, pyridinyl, pyridazinyl, pyrimidinyl, pyrazinyl, indolyl, indazolyl, benzo[b]thienyl, quinolinyl, isoquinolinyl or quinazolinyl.

Whenever the term "alkyl" or "aryl" or either of their prefix roots appear in a name of a substituent (e.g., aryl($C_{1-6}$)alkyl) it shall be interpreted as including those limitations given above for "alkyl" and "aryl." Designated numbers of carbon atoms (e.g., $C_{1-6}$) shall refer independently to the number of carbon atoms in an alkyl or cycloalkyl moiety or to the alkyl portion of a larger substituent in which alkyl appears as its prefix root.

The term "halogen" shall include iodine, bromine, chlorine and fluorine.

The novel substituted aminoquinuclidine compounds of the present invention are useful δ-opioid receptor modulators. In particular, the instant aminoquinuclidine compounds include δ-opioid receptor agonists useful as analgesics. Examples of pain intended to be within the scope of the present invention include, but are not limited to, centrally mediated pain, peripherally mediated pain, structural or soft tissue injury related pain, progressive disease related pain, neuropathic pain and acute pain such as caused by acute injury, trauma or surgery and chronic pain such as caused by neuropathic conditions, diabetic peripheral neuropathy, post-herpetic neuralgia, trigeminal neuralgia, post-stroke pain syndromes or cluster or migraine headaches. The utility of the instant compounds as δ-opioid receptor agonists can be determined according to the procedures described herein.

Also, certain compounds of the present invention are δ-opioid receptor antagonists useful as immunosuppressants, antiinflammatory agents, agents for the treatment of neurological and psychiatric conditions, medicaments for drug and alcohol abuse, agents for treating gastritis and diarrhea, cardiovascular agents and agents for the treatment of respiratory diseases, having reduced side-effects. The utility of the instant compounds as δ-opioid receptor antagonists can be determined by those skilled in the art using established animal models.

An embodiment of the invention is a pharmaceutical composition comprising one or more compounds of this invention in association with a pharmaceutically acceptable carrier. Another embodiment is a pharmaceutical composition made by mixing any of the compounds described above and a pharmaceutically acceptable carrier. A further embodiment is a process for making a pharmaceutical composition comprising mixing any of the compounds described above and a pharmaceutically acceptable carrier.

The present invention includes a method for treating a disorder modulated by the δ-opioid receptor. An embodiment of the present invention is a method for treating pain modulated by a δ-opioid agonist. Another embodiment is a method for treating immune disorders, inflammation, neurological conditions, psychiatric conditions, drug abuse, alcohol abuse, gastritis, diarrhea, cardiovascular disorders or respiratory disorders modulated by a δ-opioid antagonist.

The present invention therefore provides a method for the use of the instant substituted aminoquinuclidine compounds as δ-opioid receptor modulators in a subject in need thereof which comprises administering any of the compounds as defined herein in a therapeutically effective dose to modulate the δ-opioid receptor. A compound may be administered to a subject in need of treatment by any conventional route of administration including, but not limited to oral, nasal, sublingual, ocular, transdermal, rectal, vaginal and parenteral (i.e. subcutaneous, intramuscular, intradermal, intravenous etc.).

A therapeutically effective dose for use of the instant compounds or a pharmaceutical composition thereof comprises a dose range of from about 0.001 mg to about 1,000 mg, in particular from about 0.1 mg to about 500 mg or, more particularly from about 1 mg to about 250 mg of active ingredient per day for an average (70 kg) human.

For oral administration, a pharmaceutical composition is preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated. Advantageously, compounds of the present invention may be administered in a single daily dose or the total daily dosage may be administered in divided doses of two, three or four times daily.

It is apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level.

Compounds of this invention may be administered in any of the foregoing compositions and dosage regimens or by means of those compositions and dosage regimens established in the art whenever use of the compounds of the invention as δ-opioid receptor modulators is required for a subject in need thereof.

The terms used in describing the invention are commonly used and known to those skilled in the art. As used herein, the following abbreviations have the indicated meanings:

| Cpd | Compound |
|---|---|
| BINAP | 2,2'-Bis(diphenylphosphino)-1,1'-binaphthyl |
| DCE | 1,2-dichloroethane |
| h | Hour |
| HATU | O-(7-azabenzotriazol-1-yl)-N,N,N',N'-tetramethyluronium hexafluorophosphate |
| HBTU | 2-(1H-benzotriazole-1-yl)-1,1,3,3-tetramethyluronium hexafluorophosphate |
| min | Minute |
| $Pd_2dba_3$ | Tris(dibenzylideneacetone)-dipalladium(0) |
| rt | Room temperature |
| TLC | Thin layer chromatography |

General Synthetic Methods

Representative compounds of the present invention can be synthesized in accordance with the general synthetic methods described below and are illustrated in the schemes that follow. Since the schemes are an illustration, the invention should not be construed as being limited by the chemical reactions and conditions expressed. The preparation of the various starting materials used in the schemes is well within the skill of persons versed in the art.

Scheme A illustrates the preparation of certain target aminoquinuclidine compounds of the invention whereby a 3-quinuclidinone Compound A1 underwent reductive alkylation with an aryl amino Compound A2 in the presence of a reducing agent such as sodium triacetoxyborohydride to provide an N-substituted 3-aminoquinuclidine Compound A3. Alternatively, this reductive alkylation may be effected by reacting a 3-quinuclidinone A1 with an aryl amino compound A2 to first form the imine, which in some cases is done in the presence of Ti(iOPr)4, followed by reduction of the corresponding imine with a reducing agent such as sodium borohydride to provide an N-substituted 3-aminoquinuclidine Compound A3.

The 3-aminoquinuclidine Compound A3 then underwent a Buchwald-Hartwig arylation with a suitably substituted aryl bromide Compound A4 to give an N-phenyl-N-benzamido-3-aminoquinuclidine Compound A5.

Scheme A illustrates the method described above.

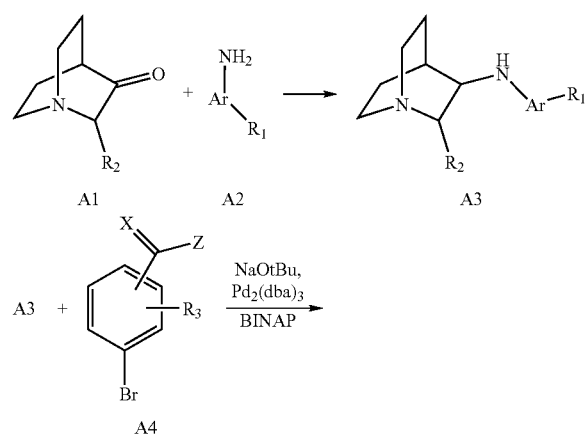

-continued

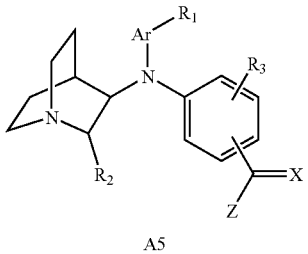

A5

Scheme B describes the preparation of certain target aminoquinuclidine compounds of the invention whereby a 3-aminoquinuclidine Compound B1 was reductively alkylated with an appropriately substituted aldehyde Compound B2 to give the N-substituted-3-aminoquinuclidine Compound B3. The 3-aminoquinuclidine Compound B3 then underwent a Buchwald-Hartwig arylation reaction to give the N-benzyl-N-4-benzamido-3-aminoquinuclidine Compound B4.

Scheme B

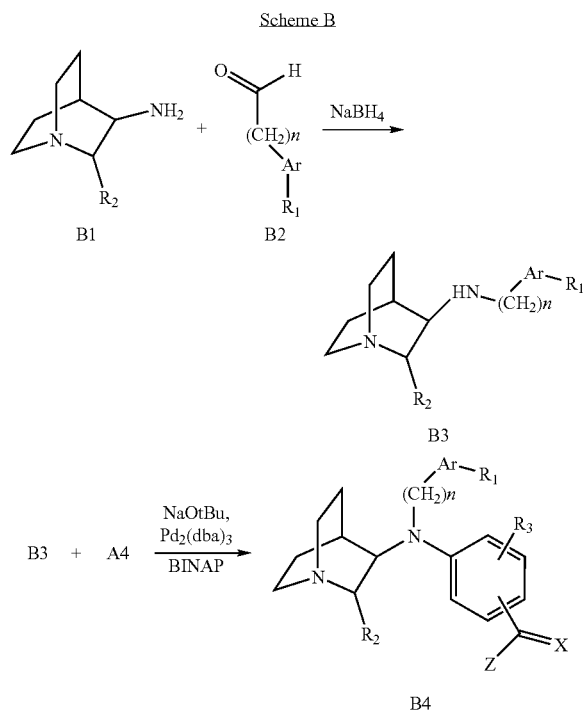

Specific Synthetic Methods

Specific compounds which are representative of the invention may be prepared as per the following examples offered by way of illustration and not by way of limitation. For the sake of clarity, bracketed numbers following compound names indicate the stoichiometric salt associated with the compound, which is further exemplified by the calculated analytical data. No attempt has been made to optimize the yields obtained in any of the reactions. One skilled in the art would know how to increase such yields through routine variations in reaction times, temperatures, solvents and/or reagents.

EXAMPLE 1

N,N-Diethyl-4-[phenyl-(1-azabicyclo[2.2.2]octan-3-amino)]benzamide Fumarate [1:1] (Compound 1)

(Method 1A) To a mixture of 9.3 g (0.1 mol) of aniline and 16.1 g (0.1 mol) of 1-azabicyclo[2.2.2]octan-3-one hydrochloride in 250 mL of dichloroethane (DCE) was added 31.8 g (0.15 mol) of $Na(OAc)_3BH$ and the mixture was stirred overnight at room temperature. The reaction was quenched with 3 N NaOH. The layers were separated and the aqueous layer was extracted with an additional portion of $CHCl_3$. The organic layers were combined, dried over $NaSO_4$, and then filtered and the solvent was evaporated in vacuo. Th residue was chromatographed on silica (95/5 $CHCl_3$/10% $NH_4OH$ in MeOH) to give N-Phenyl-1-azabicyclo[2.2.2]octan-3-amine (6.0 g 30%) as an off-white solid. $MH^+$=203. $^1H$ NMR ($CDCl_3$) 1.46 (m, 1H), 1.75 (m, 3H), 2.0 (m, 1H), 2.55 (m, 1H), 2.95 (m, 4H), 3.4 (m, 2H), 3.8 (s, 1H), 6.6 (d, 2H), 6.75 (t, 1H), 7.2 (t, 2H).

(Method 1B) A mixture of 1.26 g of 1-azabicyclo[2.2.2]octan-3-one and 0.93 g of aniline and 4.4 mL of $Ti(/PrO)_4$ was stirred overnight at room temperature. The reaction mixture was diluted with EtOH and then $NaBH_4$ pellets (0.8 g) were added until reaction was judged complete by TLC. The solvent was evaporated in vacuo. The residue was diluted with 3N NaOH, water and EtOAc and the mixture was filtered through dicalite. The filter pad was washed with additional EtOAc. The filtrate was transferred to a separatory funnel and the aqueous layer was extracted with an additional portion of EtOAc. The combined organic extracts were washed with water and then brine and then dried over $K_2CO_3$. The solution was filtered and the solvent was evaporated in vacuo. The residue was chromatographed on silica (90/7.5/2.5 $CHCl_3$/MeOH/7.0 M $NH_3$ in MeOH) to give N-Phenyl-1-azabicyclo[2.2.2]octan-3-amine (1.5 g, 75%) as a white solid. $^1H$ NMR ($CDCl_3$) is consistent with the one from Method 1A.

A solution of 0.5 g (2.5 mmol) of N-phenyl-1-azabicyclo[2.2.2]octan-3-amine, 0.64 g (2.5 mmol) of N,N-diethyl-4-bromobenzamide, 23 mg (0.025 mmol) of tris(dibenzylideneacetone)-dipalladium(0) ($Pd_2(dba)_3$), and 47 mg (0.075 mmol) of BINAP and 0.36 g (3.75 mmol) of NaOtBu in 5 mL of dry toluene was heated at 100–150° C. for 16 hrs. The reaction mixture was cooled and diluted with water and EtOAc. The aqueous layer was extracted with a second portion of EtOAc and the combined extracts were washed with water and then with brine and then dried over $K_2CO_3$. The solution was filtered and the solvent was evaporated in vacuo. The residue was chromatographed on silica (96/4 $CHCl_3$/10% $NH_4OH$ in MeOH). The appropriate fractions were combined and the solvent was evaporated in vacuo. The residue was combined with 1 eq. of fumaric acid in 2-PrOH. The solvent was evaporated in vacuo and the residue recrystallized from acetone to give Compound 1 (0.45 g, 37%) as a white solid mp 181–183° C. $MH^+$=378. $^1H$ NMR (DMSO-$d_6$) 1.05 (t, 6H), 1.35 (m, 1H), 1.65 (m, 1H), 1.8 (m, 2H), 2.05 (br s, 1H), 2.7 (m, 2H), 3.0 (m, 4H), 3.3 (br s, 4H), 3.55 (t, 1H), 4.3 (t, 1H), 6.45 (s, 2H), 6.8 (d, 2H), 7.2 (m, 5H), 7.4 (t, 2H). Anal. Calcd for $C_{24}H_{31}N_3O \cdot C_4H_4O_4$: C, 68.13; H, 7.15; N, 8.51. Found C, 67.81; H, 7.03; N, 8.40.

EXAMPLE 2

N,N-Diethyl-4-[(3-methoxyphenyl)-(1-azabicyclo[2.2.2]octan-3-amino)]benzamide Fumarate Hydrate [1:1:0.5] (Compound 2)

(Method 2A) A solution of 1-azabicyclo[2.2.2]octan-3-one (8.1 g, 50 mmol), m-anisidine (6.2 g, 50.0 mmol) and 4Å molecular sieves in 50 mL of EtOH was stirred at room temperature overnight. NaBH$_4$ pellets were added until the reaction was judged complete by TLC, at which point most of the EtOH was evaporated in vacuo and the residue was partitioned between 3N NaOH and EtOAc. The aqueous layer was extracted with a second portion of EtOAc. The organic layers were combined and washed with water and then brine and then dried over NaSO$_4$. The solution was filtered and the solvent was evaporated in vacuo. The residue was dissolved in 2-PrOH and treated with 1.5 g of fumaric acid. The product was collected and recrystallized from 2-PrOH to give N-(3-methoxyphenyl)-1-azabicyclo[2.2.2]octan-3-amine (5.2 g, 30%) as an intermediate, an off-white solid. MH$^+$=233.

Using the same procedure as described above for Compound 1 and the intermediate N-(3-methoxyphenyl)-1-azabicyclo[2.2.2]octan-3-amine in place of N-phenyl-1-azabicyclo[2.2.2]octan-3-amine, a crude product was obtained and chromatographed on silica (97/3 CHCl$_3$/10% NH$_4$OH in MeOH). The appropriate fractions were combined and the solvent was evaporated in vacuo. The free base obtained was treated with 1 eq of fumaric acid in 2-PrOH. After evaporating the solvent in vacuo the residue was triturated with Et$_2$O to give 0.18 g (6% yield) of Compound 2 as an amorphous solid: MH$^+$=408. $^1$H NMR (DMSO-d$_6$) 1.05 (t, 6H), 1.35 (m, 1H), 1.75 (m, 3H), 2.05 (br s, 1H), 2.7 (m, 1H), 2.95 (m, 4H), 3.3 (br s, 4H), 3.45 (m, 1H), 3.7 (s, 3H), 4.2 (m, 1H), 6.45 (s, 2H), 6.8 (m, 5H), 7.3 (m, 3H). Anal. Calcd for C$_{25}$H$_{33}$N$_3$O$_2$.C$_4$H$_4$O$_4$.0.5H$_2$O: C, 65.40; H, 7.19; N, 7.89. Found C, 65.60; H, 7.13; N, 7.67.

EXAMPLE 3

N,N-Diethyl-4-[(3-hydoxyphenyl)-(1-azabicyclo[2.2.2]octan-3-amino)]benzamide Fumarate Hydrate [1:1:0.5] (Compound 3)

To a solution of N,N-Diethyl-4-[(3-methoxyphenyl)-(1-azabicyclo[2.2.2]octan-3-amino)]benzamide fumarate hydrate (Compound 2)(0.3 g, 0.74 mmol) in CH$_2$Cl$_2$ cooled to −78° C. was added BBr$_3$ (4.5 ml, 4.45 mmol) and the reaction mixture was allowed to gradually warm to room temperature overnight. The reaction was quenched with ice/NaHCO$_3$ and the mixture was then heated at reflux for 4 hrs. The reaction mixture was extracted with CHCl$_3$, dried over K$_2$CO$_3$, filtered and the solvent was evaporated in vacuo. Th residue was chromatographed on silica 93/7 (CHCl$_3$/10% NH$_3$ in MeOH). The appropriate fractions were combined and the solvent was evaporated and the residue was combined with 1 eq. of fumaric acid in MeOH. The solution was filtered and the solvent evaporated to give Compound 3 (0.085 g, 23%) as a semisolid. MH$^+$=394.

EXAMPLE 4

N,N-Diethyl-4-[(3-trifluoromethylphenyl)-(1-azabicyclo[2.2.2]octan-3-amino)]benzamide Hydrochloride [1:1] (Compound 4)

Using method 1A and THF as the solvent and m-trifluoromethylaniline in place of aniline, a crude product was obtained and was purified by chromatography on silica (97/3 CHCl$_3$/10% NH$_4$OH in MeOH) to give N-(3-trifluoromethylphenyl)-1-azabicyclo[2.2.2]octan-3-amine as an intermediate (1.3 g, 10% yield), a pale yellow solid. MH$^+$=271.

Using the procedure described above for Compound 1 and N-(3-trifluoromethylphenyl)-1-azabicyclo[2.2.2]octan-3-amine in place of N-phenyl-1-azabicyclo[2.2.2]octan-3-amine, a crude product was obtained and chromatographed on silica (97/3 CHCl$_3$/10% NH$_4$OH in MeOH). The appropriate fractions were combined and the solvent was evaporated in vacuo. The residue was dissolved in Et$_2$O and treated with Et$_2$O.HCl. A solid was collected and recrystallized from acetone to give Compound 4 (0.15 g, 12%) as a white solid. MH$^+$=487. $^1$H NMR (DMSO-d$_6$) 1.1 (br s, 6H), 1.65 (m, 2H), 1.95 (m, 2H), 2.15 (br s, 1H), 3,3 (m, 8H), 3.8 (m, 1H), 4.45 (m, 1H), 7.15 (d, 2H), 7.4 (m, 5H), 7.55 (t, 1H). Anal. Calcd for C$_{25}$H$_{30}$F$_3$N$_3$O$_2$.HCl: C, 62.30; H, 6.48; N, 8.72. Found C, 61.77; H, 6.33; N, 8.38.

EXAMPLE 5

N,N-Diethyl-4-[(2-methoxyphenyl)-(1-azabicyclo[2.2.2]octan-3-amino)]benzamide Hydrochloride [1:1] (Compound 5)

Using Method 1B and o-anisidine in place of aniline, a crude product was produced and was chromatographed on silica (97/3 CHCl$_3$/10% NH$_4$OH in MeOH) to give N-(2-Methoxyphenyl)-1-azabicyclo[2.2.23octan-3-amine (1.5 g, 13%) as an intermediate, an oil.

Using the same procedure as described for Compound 1 and N-(2-methoxyphenyl)-1-azabicyclo[2.2.2]octan-3-amine in place of N-phenyl-1-azabicyclo[2.2.2]-octan-3-amine, a crude product was obtained and chromatographed on silica (94/6 CHCl$_3$/0.5 M NH$_3$ in MeOH). The appropriate fractions were combined and the solvent was evaporated in vacuo. The residue was dissolved in EtOAc and treated with Et$_2$O.HCl to give Compound 5 (0.06 g, 2%) as a white solid. MH$^+$=408. $^1$H NMR DMSO-d$_6$) 1.05 (t, 6H), 1.55 (m, 1H), 1.7 (m, 1H), 1.9 (m, 1H), 2.05 (m, 1H), 2.2 (s, 1H), 2.9 (m, 1H), 3.1 (t, 2H), 3.3 (m, 6H), 3.7 (s, 3H), 3.8 (t, 1H), 4.45 (t, 1H), 6.55 (d, 2H), 7.05 (t, 1H), 7.15 (m, 3H), 7.4 (m, 2H), 10.1 (br s, 1H).

EXAMPLE 6

N,N-Diethyl-4-[(3-chlorophenyl)-(1-azabicyclo[2.2.2]octan-3-amino)]benzamide Hydrochloride [1:1] (Compound 6)

Using Method 1B and 3-chloroaniline was in place of aniline a crude product was obtained and chromatographed on silica (95/5 CHCl$_3$/0.5 M NH$_3$ in MeOH) to give N-(3-chlorophenyl)-1-azabicyclo[2.2.2]octan-3-amine (1.5 g, 13%) as an intermediate, an oil. MH$^+$=237.

Using the same procedure as described for Compound 1 and N-(3-chlorophenyl)-1-azabicyclo[2.2.2]octan-3-amine in place of N-phenyl-1-azabicyclo[2.2.2]octan-3-amine, a crude product was obtained and chromatographed on silica (95/5 CHCl₃/1.0 M NH₃ in MeOH). The appropriate fractions were combined and the solvent was evaporated in vacuo. This residue was dissolved in EtOAc and treated with Et₂O.HCl to provide Compound 6 (0.083 g, 7%) as a white solid. MH⁺=412, 414. ¹H NMR (DMSO-d₆) 1.05 (t, 6H), 1.5 (m, 1H), 1.75 (m, 1H), 1.9 (m, 2H), 2.1 (sl br s, 1H), 2.9 (q, 1H), 3.4 (m, 8H), 3.8 (t, 1H), 4.4 (t, 1H), 7.1 (m, 3H), 7.5 (m, 2H), 7.35 (m, 3H).

EXAMPLE 7

N,N-Diethyl-4-[(3,5-dichlorophenyl)-(1-azabicyclo [2.2.2]octan-3-amino)]benzamide Hydrochloride [1:1] (Compound 7)

Using Method 1B and 3,5-dichloroaniline in place of aniline, a crude product was obtained and chromatographed on silica (92/8 CHCl₃/0.5 M NH₃ in MeOH) to give N-(3,5Dichlorophenyl)-1-azabicyclo[2.2.2]octan-3-amine (1.6 g, 12%) as an intermediate, an off-white solid. MH⁺=271, 273, 275.

Using the same procedure as described for Compound 1 and N-(3,5-dichlorophenyl-1-azabicyclo[2.2.2]octan-3-amine in place of N-phenyl-1-azabicyclo[2.2.2]octan-3-amine, a crude product was obtained and chromatographed on silica (96/4 CHCl₃/0.5 M NH₃ in MeOH). The appropriate fractions were combined and the solvent was evaporated in vacuo. The residue was dissolved in acetone and treated with Et₂O.HCl. The product was collected by filtration and recrystallized from MeCN to give Compound 7 (0.67 g, 46%) as a white solid. MH⁺=446, 448, 450. ¹H NMR (DMSO-d₆) 1.1 (t, 6H), 1.45 (m, 2H), 1.9 (m, 2H), 2.s (s, 1H), 3.0 (q, 1H), 3.4 (m, 8H), 3.85 (t, 1H), 4.45 (t, 1H), 6.9 (s, 2H), 7.15 (s, 1H), 7.35 (d, 2H), 7.45 (d, 2H). Anal. Calcd for C₂₄H₂₉Cl₂N₃O.HCl: C, 59.70; H, 6.26; N, 8.70. Found C, 59.52; H, 6.24; N, 8.89.

EXAMPLE 8

N,N-Diethyl-4-[phenyl-(trans-2-methyl-1-azabicyclo [2.2.2]octan-3-amino)]benzamide Fumarate Hydrate [1:1:0.5] (Compound 8)

A mixture of 10.1 g (58.4 mmol) of 2-methylene-1-azabicyclo[2.2.2]octan-3-one hydrochloride hydrate, 8.1 g of K₂CO₃ and 100 mg of PtO₂ in 100 mL of MeOH was hydrogenated at 10–15 psi H₂ for about 1 hr. The solution was filtered through dicalite and the solvent was evaporated in vacuo. The residue was dissolved in CHCl₃ and again filtered through dicalite. The filtrate was evaporated in vacuo to give 4.7 g (58% yield) of 2-methyl-1-azabicyclo[2.2.2] octan-3-one Compound 8A as a yellow oil. ¹H NMR (CDCl₃) 1.3 (d, 3H), 2.0 (m, 4H), 2.4 (t, 1H), 2.9 (m, 1H), 3.05 (, 1H), 3.2 (m, 3H). This material was used without further purification in the next step.

Using method 1B and 2-methyl-1-azabicyclo[2.2.2]octan-3-one Compound 8A in place of 1-azabicyclo[2.2.2] octan-3-one a crude product was obtained and chromatographed on silica (92/8 CHCl₃/0.5 M NH₃ in MeOH) to obtain 3.6 g of product as a mixture of diastereomers. A second chromatography (75/25 EtOAc/0.5 M NH₃ in MeOH) gave trans-2-methyl-N-phenyl-1-azabicyclo[2.2.2] octan-3-amine Compound 8B (0.56 g, 4%) as a light yellow oil. MH⁺=217. ¹H NMR (CDCl₃) 1.25 (d, 3H), 1.4 (m, 1H), 1.7 (m, 3H), 2.05 (d, 1H), 2.5 (m, 1H), 2.7 (m, 1H), 3.0 (m, 4H), 3.65 (d, 1H), 6.6 (d, 2H), 6.7 (t, 1H), 7.2 (t, 2H). Cis-2-methyl-N-phenyl-1-azabicyclo[2.2.2]octan-3-amine Compound 8C was also isolated.

Using the same procedure as described for Compound 1 and N-phenyl-(trans-2-methyl-1-azabicyclo[2.2.2]octan-3-amine) Compound 8B in place of N-phenyl-1-azabicyclo [2.2.2]octan-3-amine a crude product was obtained and chromatographed on silica (96/4 CHCl₃/0.5 M NH₃ in MeOH). The appropriate fractions were combined and the solvent was evaporated in vacuo. The residue obtained was combined with 1 eq. of fumaric acid in 2-PrOH. The solvent was evaporated in vacuo and the residue was triturated with EtOAc to provide Compound 8 (0.22 g, 21%) as an off-white solid. MH⁺=392. ¹H NMR (DMSO-d₆) 1.1 (t, 6H), 1.2 (d, 3H), 1.45 (m, 1H), 1.6 (m, 1H), 1.7 (m, 1H), 1.95 (m, 1H), 2.3 (br s, 1H), 2.9 (m, 4H), 3.35 (m, 5H), 3.9 (d, 1H), 6.5 (s, 2H), 6.7 (d, 2H), 7.2 (t, 4H), 7.3 (t, 1H), 7.5 (t, 2H). Anal. Calcd for C₂₅H₃₃N₃O.C₄H₄O₄.0.5H₂O: C, 67.42; H, 7.41; N, 8.13. Found C, 67.61; H, 7.29; N, 7.85.

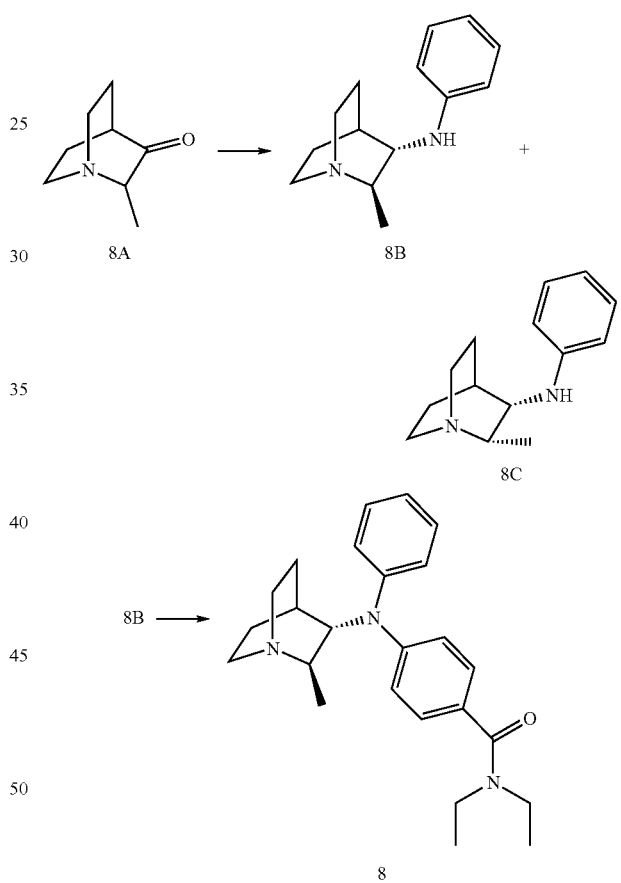

EXAMPLE 9

N,N-Diethyl-4-[phenyl-(cis-2-methyl-1-azabicyclo [2.2.2]octan-3-amino)]benzamide (Compound 9)

Cis-2-Methyl-N-Phenyl-1-azabicyclo[2.2.2]octan-3-amine Compound 8C was also isolated from the mixture of diastereomers described in Example 8. MH⁺=217. ¹H NMR (CDCl₃) 1.25 (d, 3H), 1.4 (m, 1h), 1.7 (m, 4H), 1.9 (m, 1H), 2.7 (m, 1H), 2.9 (m, 2H), 3.1 (m, 1H), 3.35 (m, 1H), 3.55 (t, 1H), 4.0 (d, 2H), 6.55 (d, 2H), 6.7 (t, 1H), 7.2 (t, 2H).

Using the same procedure as described above for Compound 1 and N-phenyl-(cis-2-methyl-1-azabicyclo[2.2.2]octan-3-amine) Compound 8C in place of N-phenyl-1-azabicyclo[2.2.2]octan-3-amine, a crude product was obtained and chromatographed on silica (92/8 CHCl$_3$/0.5 M NH$_3$ in MeOH) to give Compound 9 (0.024 g, 3%). MH$^+$=392. $^1$H NMR (DMSO-d$_6$) 0.9 (m, 2H), 1.3 (m, 10H), 1.7 (br s, 4H), 2.0 (s, 1H), 2.5 (m, 1H), 3.05 (m, 2H), 3.5 (br s, 2H), 3.7 (t, 1H), 3.95 (d, 1H), 6.5 (d, 2H), 7.15 (d, 2H), 7.25 (m, 3H), 7.4 (m, 2H).

EXAMPLE 10

N,N-Diethyl-4-[(3-thiomethylphenyl)-(trans-2-methyl-1-azabicyclo[2.2.2]octan-3-amino)]benzamide Fumarate [1:1.5] (Compound 10)

Using the procedure of Example 8 and 3-thiomethylaniline in place of aniline, a crude product was obtained and chromatographed on silica (75/25 EtOAc/0.5 M NH$_3$ in MeOH) to give trans-2-methyl-N-(3-thiomethylphenyl)-1-azabicyclo[2.2.2]octan-3-amine as an intermediate (0.4 g, 4%). MH$^+$=263.

Using the same procedure as described above for Compound 1 and N-(3-thiomethylphenyl)-(trans-2-methyl-1-azabicyclo[2.2.2]octan-3-amine) in place of N-phenyl-1-azabicyclo[2.2.2]octan-3-amine, a crude product was obtained and chromatographed on silica (94/6 CHCl$_3$/0.5 M NH$_3$ in MeOH). The appropriate fractions were combined and the solvent was evaporated in vacuo. The residue was combined with 1 eq of fumaric acid in 2-PrOH and then the solvent was evaporated in vacuo. The residue was triturated with EtOAc to give Compound 10 (0.26 g, 9%) as a beige solid mp 163–165° C. MH$^+$=438. $^1$H NMR (DMSO-d$_6$) 1.1 (t, 6H), 1.2 (d, 4H), 1.5 (m, 2H), 1.75 (m, 1H), 2.05 (m, 1H), 2.5 (s, 3H), 2.95 (m, 3H), 3.05 (m, 1H), 3.3 (m, 5H), 3.95 (d, 1H), 6.5 (s, 3H), 6.85 (d, 2H), 6.95 (m, 2H), 7.15 (d, 1H), 7.25 (d, 2H), 7.4 (t, 1H). Anal. Calcd for C$_{26}$H$_{35}$N$_3$OS.1.5C$_4$H$_4$O$_4$: C, 62.83; H, 6.76; N, 6.87. Found C, 62.76; H, 6.87; N, 6.75.

EXAMPLE 11

N,N-Diethyl-4-[phenyl-(1-azabicyclo[2.2.2]octan-3-amino)]-3-fluorobenzamide Fumarate [1:1] (Compound 11)

To a solution of 20.0 g (0.091 moles) of 2-fluoro-4-bromo-benzoic acid in 200 mL of benzene was added 40 mL of SOCl$_2$ and the mixture was heated at reflux overnight. The solvent and excess SOCl$_2$ was evaporated in vacuo. The residue was taken up in benzene and again evaporated in vacuo (2×) to remove SOCl$_2$. The residue was dissolved in CH$_2$Cl$_2$ and added in one portion to a mixture of 100 mL HNEt$_2$ in dil NaOH/ice/CH$_2$Cl$_2$. After stirring for an hour, the mixture was transferred to a separatory funnel and the aqueous layer was extracted with a second portion of CH$_2$Cl$_2$. The organic layers were combined and washed with water and then brine and then dried over NaSO$_4$. The solution was filtered and the filtrate was evaporated in vacuo. The residue was recrystallized from hexane to obtain N,N-diethyl-2-fluoro-4-bromobenzamide (13.2 g, 52%) as an intermediate, a cream colored solid. $^1$H NMR (CDCl$_3$) 1.05 (t, 3H), 1.25 (t, 3H), 3.2 (q, 2H), 3.55 (q, 2H), 7.25 (m, 3H).

Using the same procedure as described above for Compound 1 and N,N-diethyl-2-fluoro-4-bromobenzamide in place of N,N-diethyl-4-bromobenzamide, a crude product was obtained and chromatographed on silica (95/5 CHCl$_3$/0.5 M NH$_3$ in MeOH). The appropriate fractions were combined and the solvent was evaporated in vacuol. The residue was combined with 1 eq of fumaric acid in 2-PrOH and then the solvent was evaporated in vacuo. The residue was recrystallized from acetone to give Compound 11 (0.5 g, 39%). MH$^+$=396. $^1$H NMR (DMSO-d$_6$) 0.95–1.25 (2m, 6H), 1.4 (m, 2H), 1.7–2.0 (2m, 2H), 2.7–3.3 (m, 8H), 3.6 (d, 2H), 3.6 (t, 1H), 4.25 (t, 1H), 6.5 (m, 4H), 7.1 (t, 1H), 7.35 (d, 2H), 7.4 (m, 1H), 7.55 (m, 2H). Anal. Calcd for C$_{24}$H$_{30}$FN$_3$O.C$_4$H$_4$O$_4$: C, 65.74; H, 6.70; N, 8.21. Found C, 65.65; H, 6.69; N, 8.21.

EXAMPLE 12

N,N-Diethyl-4-[phenyl-(1-azabicyclo[2.2.2]octan-3-amino)]-3-methylbenzamide Fumarate [1:1] (Compound 12)

Using the same procedure as described above for Compound 1 and N,N-diethyl-2-methyl-4-bromobenzamide in place of N,N-diethyl-4-bromobenzamide, a crude product was obtained and chromatographed on silica (94/6 CHCl$_3$/0.5 M NH$_3$ in MeOH). The appropriate fractions were combined and the solvent was evaporated in vacuo. The residue was combined with 1 eq of fumaric acid in 2-PrOH. The solvent was evaporated in vacuo and the residue was triturated with acetone to give Compound 12 (0.74 g, 58%) as a white solid mp 184–186° C. MH$^+$=392. $^1$H NMR (DMSO-d$_6$) 0.95 (t, 3H), 1.15 (t, 3H), 1.35 (m, 1H), 1.75 (m, 3H), 1.75 (m, 3H), 1.9 (s, 1H), 2.1 (s, 3H), 2.65 (dd, 1H), 2.9 (m, 6H), 3.45 (m, 3H), 4.15 (t, 1H), 6.5 (s, 2H), 6.8 (m, 2H), 7.05 (d, 1H), 7.15 (m, 3H), 7.4 (t, 2H). Anal. Calcd for C$_{25}$H$_{33}$N$_3$O.C$_4$H$_4$O$_4$: C, 67.88; H, 7.56; N, 8.19. Found C, 67.93; H, 7.29; N, 7.98.

EXAMPLE 13

N,N-Diethyl-4-[phenyl-(1-azabicyclo[2.2.2]octan-3-amino)]-3-chlorobenzamide Fumarate [1:1] (Compound 13)

Using the same procedure as described above for Compound 1 and N,N-diethyl-2-chloro-4-bromobenzamide in place of N,N-diethyl-4-bromobenzamide, a crude product was obtained and chromatographed on silica (93/7 CHCl$_3$/1.0 M NH$_3$ in MeOH). The appropriate fractions were combined and the solvent was evaporated in vacuo. The residue was combined with 1 eq of fumaric acid in 2-PrOH and then the solvent was evaporated in vacuo and the residue was recrystallized from acetonitrile to give Compound 13 (1.17 g, 44%). MH$^+$=412, 414. $^1$H NMR (DMSO-d$_6$) 1.0 (t, 3H), 1.15 (t, 3H), 1.35 (m, 1H), 1.55 (m, 1H), 1.85 (m, 2H), 2.7 (m, 1H), 2.85 (m, 2H), 3.0 (m, 6H), 3.55 (m, 2H), 4.25 (t, 1H), 6.55 (s, 2H), 6.75 (m, 2H), 7.15 (d, 1H), 7.35 (m, 3H), 7.5 (m, 2H). Anal. Calcd for C$_{24}$H$_{30}$ClN$_3$O.C$_4$H$_4$O$_4$: C, 63.69; H, 6.49; N, 7.96. Found C, 63.68; H, 6.64; N, 8.14.

EXAMPLE 14

N-pyrrolidinyl-4-[(4-methoxyphenyl)-(1-azabicyclo[2.2.2]octan-3-amino)]benzamide Fumarate [1:1] (Compound 14)

Using method 1A and p-anisidine in place of aniline, a crude product was obtained and purified by chromatography (98/2 CHCl₃/10% NH₄OH in MeOH) to obtain N-(3-methoxyphenyl)-1-azabicyclo[2.2.2]octan-3-amine as an intermediate, a tan solid. MH⁺=233.

Using the same procedure as described above for Compound 1 and N-(4-methoxyphenyl)-1-azabicyclo[2.2.2]octan-3-amine in place of N-phenyl-1-azabicyclo[2.2.2]octan-3-amine and N-pyrrolidinyl-4-bromobenzamide in place of N,N-diethyl-4-bromobenzamide, a crude product was obtained and chromatographed on silica (96/4 CHCl₃/10% NH₄OH in MeOH). The appropriate fractions were combined and the solvent was evaporated in vacuo. The residue was combined with 1 eq of fumaric acid in 2-PrOH and the solvent was evaporated in vacuo. A solid was collected and recrystallized from MeCN to give Compound 14 (0.25 g, 10%). MH⁺=406. ¹H NMR (DMSO-d₆) 1.35 (br s, 2H), 1.55 (br s, 2H), 1.8 (br s, 8H), 2.05 (s, 2H), 2.9 (m, 5H), 3.45 (m, 5H), 3.85 (s, 3H), 4.2 (m, 1H), 6.45 (s, 2H), 6.55 (d, 2H), 7.0 (d, 2H), 7.2 (d, 2H), 7.4 (d, 2H).

EXAMPLE 15

N-Morpholino-4-[phenyl-(1-azabicyclo[2.2.2]octan-3-amino)]benzamide Fumarate [1:1] (Compound 15)

Using the same procedure described above for Compound 1 and N-morpholino-4-bromobenzamide in place of N,N-diethyl-4-bromobenzamide, a crude product was obtained and purified by chromatography on silica (96/4 CHCl₃/10% NH₄OH in MeOH). The appropriate fractions were combined and the solvent was evaporated in vacuo. The residue was combined with 1 eq of fumaric acid in 2-PrOH and then the solvent was evaporated in vacuo and the residue was recrystallized from MeCN to give Compound 15 (0.31 g, 24%) as a white solid mp 181–183° C. MH⁺=392. ¹H NMR (DMSO-d₆) 1.4 (m, 1H), 1.65 (m, 1H), 1.9 (m, 2H), 2.7 (m, 1H), 2.95 (m, 4H), 3.5 (m, 10H), 4.25 (m, 1H), 6.5 (s, 2H), 6.8 (d, 2H), 7.3 (m, 5H), 7.45 (m, 2H). Anal. Calcd for C₂₄H₂₉N₃O₂.C₄H₄O₄: C, 66.26; H, 6.55; N, 8.26. Found C, 65.46; H, 6.46; N, 8.11.

EXAMPLE 16

N,N-Diethyl-4-[phenylmethyl-(1-azabicyclo[2.2.2]octan-3-amino)]benzamide Fumarate Hydrate [1:1.5:1] (Compound 16)

To a solution of 3-aminoquinuclidine dihydrochloride (8.0 g, 40.0 mmol) in EtOH (100 mL) was added excess Na₂CO₃ and the mixture was stirred for 1 h and then filtered. To this solution was added benzaldehyde (3.2 g, 30.0 mmol) and the reaction was stirred at room temperature for 2 h and then NaBH₄ (3 pellets, 0.4 g ea.) was added and the reaction was stirred overnight at room temperature. The solvent was evaporated in vacuo and the residue was partitioned between 10% Na₂CO₃ and EtOAc. The organic layer was separated, dried over K₂CO₃, filtered and the solvent was evaporated in vacuo. The residue was chromatographed on silica (92/8 CHCl₃/1.0 M NH₃ in MeOH) to give N-phenylmethyl-1-azabicyclo[2.2.2]octan-3-amine (4.2 g, 76%) as an intermediate, a pale yellow oil. MH⁺=217. ¹H NMR (CDCl₃) 1.4 (m, 3H), 1.7 (m, 1H), 1.9 (m, 2H), 2.45 (2m, 1H), 2.8 (m, 5H), 3.2 (m, 1H), 3.75 (d, 2H), 7.3 (m, 5H).

Using the same procedure as described above for Compound 1 andt N-phenylmethyl-1-azabicyclo[2.2.2]octan-3-amine) in place of N-phenyl-1-azabicyclo[2.2.2]octan-3-amine, a crude product was obtained and chromatographed on silica (94/6 CHCl₃/0.5 M NH₃ in MeOH). The appropriate fractions were combined and the solvent was evaporated in vacuo. The residue was treated with 1 eq of fumaric acid and the residue was recrystallized from acetone to give Compound 16 (0.22 g, 9%) as a beige solid mp 107–110° C. MH⁺=392. ¹H NMR (DMSO d₆) 1.15 (t, 6H), 1.6 (m, 1H), 1.9 (m, 3H), 2.25 (m, 1H), 3.05 (m, 4H), 3.3 (m, 5H), 3.55 (t, 1H), 4.2 (t, 1H), 4.5 (d, 1H), 4.85 (d, 1H), 6.5 (s, 2H), 6.8 (s, 2H), 7.35 (m, 7H). Anal. Calcd for C₂₅H₃₃N₃O.1.5C₄H₄O₄.H₂O: C, 63.79; H, 7.08; N, 7.20. Found C, 63.94; H, 7.15; N, 7.09.

EXAMPLE 17

N,N-Diethyl-4-[(3-chlorophenyl)methyl)-1-azabicyclo[2.2.2]octan-3-amino)]benzamide Fumarate [1:1] (Compound 17)

A mixture of of 3-aminoquinuclidine dihydrochloride (2.0 g, 10.0 mmol), NEt₃ (1.3 mL) and 3-chlorobenzaldehyde (1.5 g, 11.0 mmol) in THF (50 mL) was stirred at room temperature. To this was added Na(OAc)₃BH 13.2 g, 15 mmol) and the reaction was stirred overnight. The reaction mixture was diluted with 3N NaOH and water and extracted with EtOAc. The organic extracts were combined, washed with water and then brine and dried over K₂CO₃. The solution was filtered and the solvent was evaporated in vacuo to give an oil which was chromatographed on silica (94/6 CHCl₃/0.5 M NH₃ in MeOH). The appropriate fractions were combined and the solvent was evaporated in vacuo to give N-[(3-chlorophenyl)methyl]-1-azabicyclo[2.2.2]octan-3-amine (0.75 g, 30%) as an intermediate, a light yellow semi-solid. MH⁺=251,253. The ¹H NMR was consistent with the assigned structure.

Using the same procedure as described above for Compound 1 and N-[(3-chlorophenyl)methyl]-1-azabicyclo[2.2.2]octan-3-amine) in place of N-phenyl-1-azabicyclo[2.2.2]octan-3-amine, a crude product was obtained and chromatographed on silica (96/4 CHCl₃/0.5 M NH₃ in MeOH). The appropriate fractions were combined and the solvent was evaporated in vacuo. The residue was combined with 1 eq of fumaric acid in 2PrOH and the solvent was evaporated n vacuo and the residue was recrystallized from acetone to give Compound 17 (0.14 g, 9%) as an off-white solid mp 193–196° C. MH⁺=426,428. ¹H NMR (DMSO d₆) 1.1 (t, 6H), 1.55 (m, 1H), 1.85 (m, 3H), 2.2 (m, 1H), 3.0 (m, 4H), 3.3 (m, 7H), 4.15 (m, 1H), 4.7 (dd, 2H), 6.5 (s, 2H), 6.85 (d, 2H), 7.3 (m, 6H). Anal. Calcd for C₂₅H₃₂ClN₃O.C₄H₄O₄: C, 64.26; H, 6.69; N, 7.75. Found C, 64.30; H, 6.54; N, 7.78.

EXAMPLE 18

N,N-Diethyl-4-[(2-fluorophenyl)methyl)-1-azabicyclo[2.2.2]octan-3-amino)]benzamide Fumarate Hydrate [1:1.5:0.75] (Compound 18)

Using the same procedure as described above for Example 17 and 2-fluorobenzaldehyde in place of 3-chlorobenzaldehyde, a crude product was obtained and chromatographed on silica (92/8 CHCl₃/0.5 M NH₃ in MeOH) to give N-[(2-fluorophenyl)methyl]-1-azabicyclo[2.2.2]octan-3-amine (0.72 g, 15%) as an intermediate, a nearly colorless oil.

Using the same procedure as described above for Compound 1 and N-[(3-chlorophenyl)methyl]-1-azabicyclo[2.2.2]octan-3-amine) in place of N-phenyl-1-azabicyclo

[2.2.2]octan-3-amine, a crude product was obtained and chromatographed on silica (96/4 $CHCl_3$/0.5 M $NH_3$ in MeOH). The appropriate fractions were combined and the solvent was evaporated in vacuo. The residue was combined with 1 eq of fumaric acid in 2-PrOH and the solvent was evaporated n vacuo and the residue was recrystallized from acetone to give Compound 18 (0.14 g, 9%) as an off-white solid mp 193–196° C. $MH^+$=410. $^1H$ NMR (DMSO-$d_6$) 1.5 (t, 6H), 1.6 (m, 1H), 1.95 (m, 3H), 3.05 (m, 4H), 3.3 (m, 5H), 3.5 (t, 1H), 4.15 (m, 1H), 4.65 (dd, 2H), 6.5 (s, 3H), 6.8 (d, 2H), 7.0–7.4 (m, 6H). Anal. Calcd for $C_{25}H_{32}FN_3O.1.5$ $C_4H_4O_4.0.75H_2O$: C, 62.35; H, 6.67; N, 7.04. Found C, 62.34; H, 6.57; N, 7.02.

EXAMPLE 19

N,N-Diethyl-4-[(3-fluorophenyl)methyl)-1-azabicyclo[2.2.2]octan-3-amino)]benzamide Fumarate [1:1] (Compound 19)

Using the same procedure as described above in Example 16 and 3-fluorobenzaldehyde in place of benzaldehyde, a crude product was obtained and chromatographed on silica (92/8 $CHCl_3$/1.0 M $NH_3$ in AeOH) to give N-[(3-fluorophenyl)methyl]-1-azabicyclo[2.2.2]octan-3-amine (1.6 g, 46%) as an intermediate, a nearly colorless oil.

Using the same procedure as described above for Compound 1 and N-[(3-fluorophenyl)methyl]-1-azabicyclo[2.2.2]octan-3-amine) in place of N-phenyl-1-azabicyclo[2.2.2]octan-3-amine, a crude product was obtained and chromatographed on silica (92/8 $CHCl_3$/1.0 M $NH_3$ in MeOH). The appropriate fractions were combined and the solvent was evaporated in vacuo. The residue was combined with 1 eq of fumaric acid in 2-PrOH and the solvent was evaporated n vacuo and the residue was recrystallized from acetone to give Compound 19 (0.28 g, 13%) as an off-white solid. MH+=410. $^1H$ NMR (DMSO-d6) 1.1 (t, 6H), 1.55 (m, 1H), 1.95 (m, 3H), 2.95 (m, 4H), 3.4 (m, 7H), 4.15 (m, 1H), 4.8 (dd, 2H), 6.5 (s, 2H), 6.8 (d, 2H), 7.05 (m, 3H), 7.25 (d, 2H), 7.35 (t, 1H).

EXAMPLE 20

(−)-(R)-N,N-Diethyl-4-[phenylmethyl-(1-azabicyclo[2.2.2]octan-3-amino)]benzamide Fumarate Hydrate [1:1.5:1] (Compound 20)

Using the same procedure as described for Example 16 except and (−)-(R)-aminoquinuclidine, ([α]=−22.1 (c=0.1, MeOH)) in place of racemic aminoquinuclidine, Compound 20 was obtained.

EXAMPLE 21

(+)-(S)-N,N-Diethyl-4-[phenylmethyl-(1-azabicyclo[2.2.2]octan-3-amino)]benzamide Fumarate Hydrate [1:1.5:1] (Compound 21)

Using the same procedure as described for Example 16 and (+)-(S)-aminoquinuclidine ([α]=17.3 (c=0.1, MeOH)) in place of racemic aminoquinuclidine, Compound 21 was obtained.

BIOLOGICAL EXAMPLES

δ-opioid and μ-opioid receptor binding for the compounds of the present invention were determined according to the following procedures and the indicated results were obtained.

Example 1

Rat Brain δ-Opioid Receptor Binding Assay

The activity of the compounds of the invention as delta receptor modulators was demonstrated by the rat brain δ-opioid receptor binding assay as described below.

Procedure

Male, Wistar rats (150–250 g, VAF, Charles River, Kingston, N.Y.) are killed by cervical dislocation, and their brains removed and placed immediately in ice cold Tris HCl buffer (50 mM, pH 7.4). The forebrains are separated from the remainder of the brain by a coronal transection, beginning dorsally at the colliculi and passing ventrally through the midbrain-pontine junction. After dissection, the forebrains are homogenized in Tris buffer in a Teflon®-glass homogenizer. The homogenate is diluted to a concentration of 1 g of forebrain tissue per 100 mL Tris buffer and centrifuged at 39,000×G for 10 min. The pellet is resuspended in the same volume of Tris buffer with several brief pulses from a Polytron homogenizer. This particulate preparation is used for the δ-opioid binding assays. Following incubation with the δ-selective peptide ligand [$^3$H]DPDPE at 25° C., the tube contents are filtered through Whatman GF/B filter sheets on a Brandel cell harvester. The tubes and filters are rinsed three times with 4 mL of 10 mM HEPES (pH 7.4), and the radioactivity associated with the filter circles determined using Formula 989 scintillation fluid (New England Nuclear, Boston, Mass.) in a scintillation counter.

Analysis

The data are used to calculate either the % inhibition compared to control binding (when only a single concentration of test compound is evaluated) or a $K_i$ value (when a range of concentrations are tested).

% Inhibition was calculated as:

$$1 - \left( \frac{\text{test compound dpm} - \text{nonspecific dpm}}{\text{total dpm} - \text{nonspecific dpm}} \right) \times 100\%;$$

$K_i$ value is calculated using the LIGAND (Munson, P. J. and Rodbard, D., Anal. Biochem. 107: 220–239, 1980) data analysis program.

Table 4 shows the biological activity in Kis for instant compounds as measured in the rat brain δ-opioid receptor binding assay.

TABLE 4

| δ-Opioid Receptor Binding ($K_i$ nM) | |
| --- | --- |
| Cpd | $K_i$ nM |
| 1 | 98 |
| 2 | 115 |
| 3 | 3 |
| 4 | <50% Inhibition at 1 μM |
| 5 | 290 |
| 6 | 171 |
| 7 | <50% Inhibition at 1 μM |
| 8 | 26 |
| 9 | 19 |
| 10 | 12 |
| 11 | 255 |

TABLE 4-continued

δ-Opioid Receptor Binding ($K_i$ nM)

| Cpd | $K_i$ nM |
|---|---|
| 12 | 608 |
| 13 | 880 |
| 14 | <50% Inhibition at 1 μM |
| 15 | <50% Inhibition at 1 μM |
| 16 | 50 |
| 17 | 21 |
| 18 | 39 |
| 19 | 5.5 |
| 20 | 11 |
| 21 | 20 |

TABLE 5

μ-Opioid Receptor Binding ($K_i$ nM)

| Cpd | $K_i$ nM |
|---|---|
| 1 | 10000 |
| 3 | 160 |
| 8 | 1340 |
| 9 | 3040 |
| 10 | 2770 |
| 11 | 8330 |
| 12 | 10000 |
| 16 | 1920 |
| 17 | 914 |
| 18 | 1160 |
| 19 | 1120 |
| 20 | 1240 |
| 21 | 2550 |

EXAMPLE 2

Rat Brain μ-Opioid Receptor Binding Assay

The activity of compounds of the invention as analgesics is demonstrated by the rat brain μ-opioid receptor binding assay as described below.

Procedure

Male, Wistar rats (150–250 g, VAF, Chades River, Kingston, N.Y.) are killed by cervical dislocation and their brains removed and placed immediately in ice cold Tris HCl buffer (50 mM, pH 7.4). The forebrains are separated from the remainder of the brain by a coronal transection, beginning dorsally at the colliculi and passing ventrally through the midbrain-pontine junction. After dissection, the forebrains are homogenized in Tris buffer in a Teflon®-glass homogenizer. The homogenate is diluted to a concentration of 1 g of forebrain tissue per 100 mL Tris buffer and centrifuged at 39,000×G for 10 min. The pellet is resuspended in the same volume of Tris buffer with several brief pulses from a Polytron homogenizer. This particulate preparation is used for the μ-opioid binding assays. Following incubation with the μ-selective peptide ligand [$^3$H]DAMGO at 25° C., the tube contents are filtered through Whatman GF/B filter sheets on a Brandel cell harvester. The tubes and filters are rinsed three times with 4 mL of 10 mM HEPES (pH 7.4) and the radioactivity associated with the filter circles determined using Formula 989 scintillation fluid (New England Nuclear, Boston, Mass.) in a scintillation counter.

Analysis

The data are used to calculate either the % inhibition compared to control binding (when only a single concentration of test compound is evaluated) or a $K_i$ value (when a range of concentrations is tested).

% Inhibition is calculated as:

$$1 - \left(\frac{\text{test compound dpm} - \text{nonspecific dpm}}{\text{total dpm} - \text{nonspecific dpm}}\right) \times 100\%;$$

$K_i$ value is calculated using the LIGAND (Munson, P. J. and Rodbard, D., Anal. Biochem. 107: 220–239, 1980) data analysis program.

Table 5 shows the biological activity as Kis for instant compounds as measured in the rat brain μ-opioid receptor binding assay.

EXAMPLE 3

Mouse Acetylcholine Bromide-Induced Abdominal Constriction Assay

The activity of compounds of the invention as analgesics was further demonstrated by the mouse acetylcholine bromide-induced abdominal constriction assay as described below.

Procedure

The mouse acetylcholine-induced abdominal constriction assay, as described by Collier et al. in *Brit. J. Pharmacol. Chem. Ther.*, 32: 295–310, 1968 with minor modifications, was used to assess analgesic potency of the compounds of formula (I). The test drugs or appropriate vehicles were administered orally (p.o.) and 30 min later the animal received an intraperitoneal (i.p.) injection of 5.5 mg/kg acetylcholine bromide (Matheson, Coleman and Bell, East Rutherford, N.J.). The mice were then placed in groups of three into glass bell jars and observed for a ten min observation period for the occurrence of an abdominal constriction response (defined as a wave of constriction and elongation passing caudally along the abdominal wall, accompanied by a twisting of the trunk and followed by extension of the hind limbs). For compounds of the present invention, the percent inhibition of this response to a nociceptive stimulus (equated to °/analgesia) was calculated as follows:

$$\% \text{ Inhibition} = \left(\frac{\text{No. of } CAR - \text{No. of } DTAR}{\text{No. of } CAR}\right) \times 100\%$$

CAR: Control Animal Responses
DTAR: Drug-Treated Animal Responses

Table 6 shows the biological activity in % inhibition at a dose of 150 μmole/Kg p.o. for instant compounds as measured in the mouse acetylcholine bromide-induced abdominal constriction (MAIT) assay.

TABLE 6

MAIT (% Inhibition)

| Cpd | % Inhibition |
|---|---|
| 1 | 55.6 |
| 9 | 20 |

TABLE 6-continued

MAIT (% Inhibition)

| Cpd | % Inhibition |
|---|---|
| 10 | 25 |
| 16 | 50 |
| 17 | 16.7 |
| 18 | 28.6 |
| 19 | 18.2 |
| 20 | 57.1 |
| 21 | 35.720 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula (I):

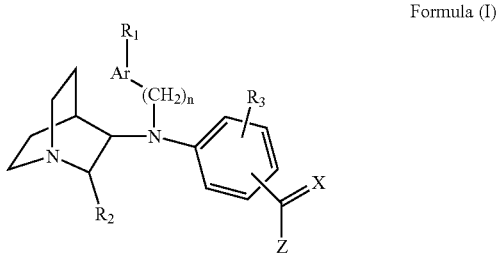

Formula (I)

wherein:

Ar is selected from the group consisting of aryl and heteroaryl;

n is an integer from 0 to 2;

$R_1$ is one to three substituents independently selected from the group consisting of hydrogen, $C_{1-8}$alkyl, $C_{2-8}$alkenyl, $C_{2-8}$alkynyl, $C_{3-8}$cycloalkyl, aryl($C_{1-8}$) alkyl, $C_{1-8}$alkoxy, aryloxy, aryl($C_{1-8}$)alkoxy, $C_{1-8}$alkylthio, trifluoro($C_{1-8}$)alkyl, trifluoro($C_{1-8}$)alkoxy, amino, —NH($C_{1-8}$)alkyl, —N[($C_{1-8}$)alkyl]$_2$, —NH(aryl), —N(aryl)$_2$, —NH($C_{1-8}$)alkylaryl, —N[($C_{1-8}$)alkylaryl]$_2$, —CO$_2$H, —CO$_2$($C_{1-8}$)alkyl, —CO$_2$(aryl), —C(O)NH$_2$, —C(O)NH($C_{1-8}$)alkyl, —C(O)N[($C_{1-8}$)alkyl]$_2$, —NHC(O)($C_{1-8}$)alkyl, —SO$_2$H, —SO$_2$($C_{1-8}$)alkyl, —SO$_2$NH$_2$, —SO$_2$NH($C_{1-8}$)alkyl, —SO$_2$N[($C_{1-8}$)alkyl]$_2$, —C(O)($C_{1-8}$)alkyl, —C(O)aryl, —C(O)($C_{1-8}$)alkylaryl, aryl, heteroaryl, heterocyclyl, halogen, hydroxy, cyano, and nitro;

$R_2$ is selected from the group consisting of hydrogen and $C_{1-8}$alkyl;

$R_3$ is selected from the group consisting of hydrogen, $C_{1-8}$alkyl, $C_{1-8}$alkoxy, $C_{1-8}$alkylthio, trifluoro($C_{1-8}$) alkyl, trifluoro($C_{1-8}$)alkoxy, amino, —NH($C_{1-8}$)alkyl, —N[($C_{1-8}$)alkyl]$_2$, —CO$_2$H, —CO$_2$($C_{1-8}$)alkyl, —C(O)NH$_2$, —C(O)NH($C_{1-8}$)alkyl, —C(O)N[($C_{1-8}$)alkyl]$_2$, —NHC(O)($C_{1-8}$)alkyl, —SO$_2$H, —SO$_2$($C_{1-8}$)alkyl, —SO$_2$NH$_2$, —SO$_2$NH($C_{1-8}$)alkyl, —SO$_2$N[($C_{1-8}$) alkyl]$_2$, —C(O)($C_{1-8}$)alkyl, halogen, hydroxy, cyano, and nitro;

X is selected from the group consisting of S and O;

Z is N($R_4$)($R_5$) or is a 5- or 6-membered saturated, monocyclic, heterocyclic ring, wherein said heterocyclic ring contains one nitrogen member which is the point of attachment, optionally contains one additional heteroatom member of oxygen, sulfur or nitrogen and optionally contains a double bond between two ring members;

$R_4$ and $R_5$ are independently selected from the group consisting of hydrogen, $C_{1-8}$alkyl, hydroxy($C_{1-8}$)alkyl, $C_{2-8}$alkenyl, $C_{3-8}$cycloalkyl, aryl and aryl($C_{1-8}$)alkyl, wherein said cycloalkyl, aryl and the aryl portion of aryl($C_{1-8}$)alkyl are optionally substituted with one to three substituents independently selected from the group consisting of $C_{1-8}$alkyl, $C_{2-8}$alkenyl, $C_{1-8}$alkoxy, trifluoro($C_{1-8}$)alkyl, trifluoro($C_{1-8}$)alkoxy, $C_{3-8}$cycloalkyl and halogen; and, the moiety —C(X)Z is attached on the phenyl at the 3 or 4 position;

and pharmaceutically acceptable enantiomers, diastereomers and salts thereof.

2. The compound of claim 1 wherein Ar is phenyl.

3. The compound of claim 1 wherein n is an integer from 0 to 1.

4. The compound of claim 1 wherein $R_1$ is independently selected from the group consisting of hydrogen, $C_{1-8}$alkyl, $C_{1-8}$alkoxy, $C_{1-8}$alkylthio, halogen, hydroxy, trifluoro($C_{1-8}$) alkyl and trifluoro($C_{1-8}$)alkoxy.

5. The compound of claim 1 wherein $R_1$ is independently selected from the group consisting of hydrogen, $C_{1-4}$alkoxy, $C_{1-4}$alkylthio, halogen, hydroxy and trifluoro($C_{1-4}$)alkyl.

6. The compound of claim 1 wherein $R_1$ is independently selected from the group consisting of hydrogen, methoxy, methylthio, chlorine, fluorine, hydroxy and trifluoromethyl.

7. The compound of claim 1 wherein $R_2$ is selected from the group consisting of hydrogen and $C_{1-4}$alkyl.

8. The compound of claim 1 wherein $R_2$ is selected from the group consisting of hydrogen and methyl.

9. The compound of claim 1 wherein $R_3$ is selected from the group consisting of hydrogen, $C_{1-8}$alkyl, halogen, trifluoro($C_{1-8}$)alkyl and trifluoro($C_{1-8}$)alkoxy.

10. The compound of claim 1 wherein $R_3$ is selected from the group consisting of hydrogen, $C_{1-4}$alkyl and halogen.

11. The compound of claim 1 wherein $R_3$ is selected from the group consisting of hydrogen, methyl and chlorine.

12. The compound of claim 1 wherein X is O.

13. The compound of claim 1 wherein Z is selected from the group consisting of N($R_4$)($R_5$) or pyrrolinyl, pyrrolidinyl, 2-imidazolinyl, imidazolidinyl, 2-pyrazolinyl, pyrazolidinyl, piperidinyl, morpholinyl, thiomorpholinyl, piperazinyl; wherein the point of attachment for the pyrrolinyl, pyrrolidinyl, 2-imidazolinyl, imidazolidinyl, 2-pyrazolinyl, pyrazolidinyl, piperidinyl, morpholinyl, thiomorpholinyl, piperazinyl ring at Z is a nitrogen ring atom.

14. The compound of claim 1 wherein Z is selected from the group consisting of N($R_4$)($R_5$), pyrrolidinyl and morpholinyl; wherein the point of attachment for the pyrrolidinyl and morpholinyl ring at Z is a nitrogen ring atom.

15. The compound of claim 1 wherein $R_4$ and $R_5$ are independently selected from the group consisting of hydrogen, $C_{1-4}$alkyl, hydroxy($C_{1-4}$)alkyl, $C_{2-4}$alkenyl, $C_{3-8}$cycloalkyl, aryl and aryl($C_{1-4}$alkyl, wherein said cycloalkyl, aryl and the aryl portion of aryl($C_{1-8}$)alkyl are optionally substituted with one to three substituents independently selected from the group consisting of $C_{1-4}$alkyl, $C_{2-4}$alkenyl, $C_{1-4}$alkoxy, $C_{3-8}$cycloalkyl, halogen, trifluoro($C_{1-4}$)alkyl and trifluoro($C_{1-4}$)alkoxy.

16. The compound of claim 1 wherein $R_4$ and $R_5$ are independently selected from the group consisting of hydrogen and $C_{1-4}$alkyl.

17. The compound of claim 1 wherein $R_4$ and $R_5$ are independently selected from the group consisting of hydrogen, methyl and ethyl.

18. The compound of claim 1 wherein the moiety —C(X)Z is substituted on the phenyl at the 4 position.

19. A compound of the Formula (Ia):

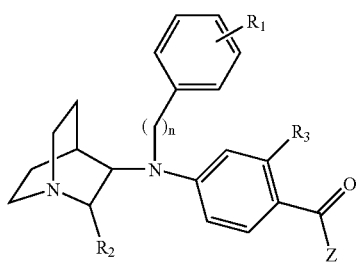

Formula (Ia)

wherein $R_1$, $R_2$, $R_3$, n and Z are selected from:

| $R_1$ | $R_2$ | $R_3$ | n | Z | Config. |
|---|---|---|---|---|---|
| H | H | H | 0 | N(Et)$_2$ | — |
| 3-OMe | H | H | 0 | N(Et)$_2$ | — |
| 3-OH | H | H | 0 | N(Et)$_2$ | — |
| 3-CF$_3$ | H | H | 0 | N(Et)$_2$ | — |
| 2-OMe | H | H | 0 | N(Et)$_2$ | — |
| 3-Cl | H | H | 0 | N(Et)$_2$ | — |
| 3,5-diCl | H | H | 0 | N(Et)$_2$ | — |
| H | trans-Me | H | 0 | N(Et)$_2$ | — |
| H | cis-Me | H | 0 | N(Et)$_2$ | — |
| 3-SMe | trans-Me | H | 0 | N(Et)$_2$ | — |
| H | H | F | 0 | N(Et)$_2$ | — |
| H | H | Me | 0 | N(Et)$_2$ | — |
| H | H | Cl | 0 | N(Et)$_2$ | — |
| 4-OMe | H | H | 0 | 1-pyrrolidinyl | — |
| H | H | H | 0 | 4-morpholinyl | — |
| H | H | H | 1 | N(Et)$_2$ | — |
| 3-Cl | H | H | 1 | N(Et)$_2$ | — |
| 2-F | H | H | 1 | N(Et)$_2$ | — |
| 3-F | H | H | 1 | N(Et)$_2$ | — |
| H | H | H | 1 | N(Et)$_2$ | R |
| H | H | H | 1 | N(Et)$_2$ | S | and pharmaceutically acceptable enantiomers, diastereomers and salts thereof.

20. A pharmaceutical composition comprising a compound of claim 1 and a pharmaceutically acceptable carrier.

21. A method for preparing a pharmaceutical composition comprising mixing a compound of claim 1 and a pharmaceutically acceptable carrier.

22. A method for treating pain in a subject in need thereof comprising administering to the subject a therapeutically effective amount of a compound of Formula (I):

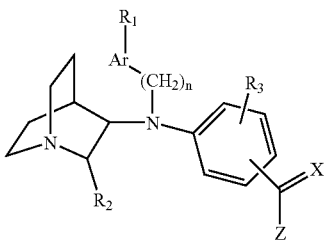

Formula (I)

wherein:

Ar is selected from the group consisting of aryl and heteroaryl;

n is an integer from 0 to 2;

$R_1$ is one to three substituents independently selected from the group consisting of hydrogen, $C_{1-8}$alkyl, $C_{2-8}$alkenyl, $C_{2-8}$alkynyl, $C_{3-8}$cycloalkyl, aryl($C_{1-8}$)alkyl, $C_{1-8}$alkoxy, aryloxy, aryl($C_{1-8}$)alkoxy, $C_{1-8}$alkylthio, trifluoro($C_{1-8}$)alkyl, trifluoro($C_{1-8}$)alkoxy, amino, —NH($C_{1-8}$)alkyl, —N[($C_{1-8}$)alkyl]$_2$, —NH(aryl), —N(aryl)$_2$, —NH($C_{1-8}$)alkylaryl, —N[($C_{1-8}$)alkylaryl]$_2$, —CO$_2$H, —CO$_2$($C_{1-8}$)alkyl, —CO$_2$(aryl), —C(O)NH$_2$, —C(O)NH($C_{1-8}$)alkyl, —C(O)N[($C_{1-8}$)alkyl]$_2$, —NHC(O)($C_{1-8}$)alkyl, —SO$_2$H, —SO$_2$($C_{1-8}$)alkyl, —SO$_2$NH$_2$, —SO$_2$NH($C_{1-8}$)alkyl, —SO$_2$N[($C_{1-8}$)alkyl]$_2$, —C(O)($C_{1-8}$)alkyl, —C(O)aryl, —C(O)($C_{1-8}$)alkylaryl, aryl, heteroaryl, heterocyclyl, halogen, hydroxy, cyano, and nitro;

$R_2$ is selected from the group consisting of hydrogen and $C_{1-8}$alkyl;

$R_3$ is selected from the group consisting of hydrogen, $C_{1-8}$alkyl, $C_{1-8}$alkoxy, $C_{1-8}$alkylthio, trifluoro($C_{1-8}$)alkyl, trifluoro($C_{1-8}$)alkoxy, amino, —NH($C_{1-8}$)alkyl, —N[($C_{1-8}$)alkyl]$_2$, —CO$_2$H, —CO$_2$($C_{1-8}$)alkyl, —C(O)NH$_2$, —C(O)NH($C_{1-8}$)alkyl, —C(O)N[($C_{1-8}$)alkyl]$_2$, —NHC(O)($C_{1-8}$)alkyl, —SO$_2$H, —SO$_2$($C_{1-8}$)alkyl, —SO$_2$NH$_2$, —SO$_2$NH($C_{1-8}$)alkyl, —SO$_2$N[($C_{1-8}$)alkyl]$_2$, —C(O)($C_{1-8}$)alkyl, halogen, hydroxy, cyano, and nitro;

X is selected from the group consisting of S and O;

Z is N($R_4$)($R_5$) or is a 5- or 6-membered saturated, monocyclic, heterocyclic ring, wherein said heterocyclic ring contains one nitrogen member which is the point of attachment, optionally contains one additional heteroatom member of oxygen, sulfur or nitrogen and optionally contains a double bond between two ring members;

$R_4$ and $R_5$ are independently selected from the group consisting of hydrogen, $C_{1-8}$alkyl, hydroxy($C_{1-8}$)alkyl, $C_{2-8}$alkenyl, $C_{3-8}$cycloalkyl, aryl and aryl($C_{1-8}$)alkyl, wherein said cycloalkyl, aryl and the aryl portion of aryl($C_{1-8}$)alkyl are optionally substituted with one to three substituents independently selected from the group consisting of $C_{1-8}$alkyl, $C_{2-8}$alkenyl, $C_{1-8}$alkoxy, trifluoro($C_{1-8}$)alkyl, trifluoro($C_{1-8}$)alkoxy, $C_{3-8}$cycloalkyl and halogen; and, the moiety —C(X)Z is attached on the phenyl at the 3 or 4 position;

and pharmaceutically acceptable enantiomers, diastereomers and salts thereof.

23. The method of claim 22 wherein the therapeutically effective amount of the compound of claim 1 is from about 0.001 mg/day to about 1000 mg/day.

24. The method of claim 23 further comprising administering to the subject a therapeutically effective amount of a pharmaceutical composition of claim 20.

25. The method of claim 22 wherein the therapeutically effective amount of the pharmaceutical composition of claim 20 is from about 0.001 mg/day to about 1000 mg/day.

* * * * *